United States Patent [19]

Mazzanobile et al.

[11] 4,108,978

[45] Aug. 22, 1978

[54] DENTAL COMPOSITIONS

[75] Inventors: Salvatore Mazzanobile, Haworth; Robert John Hillermeier, Fair Lawn, both of N.J.

[73] Assignee: Beecham Inc., Clifton, N.J.

[21] Appl. No.: 654,198

[22] Filed: Feb. 2, 1976

Related U.S. Application Data

[63] Continuation of Ser. No. 461,228, Apr. 15, 1974, abandoned, which is a continuation-in-part of Ser. No. 297,500, Oct. 13, 1972, abandoned.

[30] Foreign Application Priority Data

Oct. 20, 1971 [GB] United Kingdom ............... 48671/71

[51] Int. Cl.$^2$ ................................................ A61K 7/18

[52] U.S. Cl. .......................................... 424/49; 424/52
[58] Field of Search .................................... 424/49–58

[56] References Cited

U.S. PATENT DOCUMENTS

| 3,538,230 | 11/1970 | Pader et al. ............................ 424/52 |
| 3,689,637 | 9/1972 | Pader ................................... 424/52 X |

Primary Examiner—Shep K. Rose
Attorney, Agent, or Firm—Jacobs & Jacobs

[57] ABSTRACT

Oral hygiene compositions containing 1–50% by weight of a silica xerogel having an average particle size diameter of 25–50, preferably 25–30, microns as sole or principal polishing agent.

6 Claims, No Drawings

DENTAL COMPOSITIONS

CROSS-REFERENCE

This is a continuation of application Ser. No. 461,228, filed Apr. 15, 1974, now abandoned, which is a continuation-in-part of Ser. No. 297,500 filed Oct. 13, 1972, now abandoned.

This invention relates to oral hygiene compositions.

Oral hygiene products for use as teeth cleaning preparations consist essentially of a surfactant and a polishing agent usually formulated as a suitable liquid or semi-liquid composition. Such polishing agent assists on the removal of dental plaque and tooth surface discoloration. Other ingredients are included in such compositions for extra effect, for example anti-cariogenic, bacteriostatic, flavouring and perfumery substances. The surfactant is a wetting agent and this in combination with the polishing agent assists the removal of food particles, their decomposition products and dental plaque from the surface of the teeth. The polishing agent is thus a mild abrasive and is a finely-divided powder the hardness of which is important because if the powder is too abrasive the enamel surface of the teeth will be damaged, but if too soft an insufficient cleaning action on the teeth will result.

A wide variety of polishing agents has been proposed from time to time for use in dental compositions; those commonly employed include dicalcium phosphate, insoluble sodium metaphosphate, calcium silicate and calcium carbonate. Silica has often been proposed, but this material exists in several forms, many of which have a hardness which causes them to be too abrasive for general use.

However in U.S. Pat. No. 3,538,230 it has been proposed to make translucent and transparent dentifrices containing as the essential cleaning and polishing agent a particulate, synthetic, amorphous, porous silica xerogel in an amount from about 5 to about 50% by weight of the dentifrice. It is therein stated that these specific silicas when incorporated in dentifrices produce a high lustre after teeth brushing therewith without excessive enamel or dentin abrasion. It is also explained that these specific silicas are xerogels having a porous, almost sponge-like, particle structure in which the particle size is important. The xerogel is then further defined as generally having an average particle size diameter in the range from about 2 to about 20 microns, preferably from about 3 to about 15 microns. The specific suitable silicas recommended have average particle size diameters between 5 and 10 microns.

From the aforesaid patent specification it would be supposed that a silica xerogel of particle size materially greater than the maximum specified would be unsuitable as being too abrasive in its effect on dental enamel and dentin. However when we made oral hygiene compositions containing silica xerogels of average particle size diameter considerably greater than 20 microns, we found surprisingly on testing the action of the compositions on human dentin that the abrasive effect was quite mild and the cleaning action superior. This was doubly surprising since such compositions may possess a gritty feel which suggests before testing that the prediction of excessive abradability would hold. This gritty feel is actually an advantage since in a clear gel toothpaste the clarity suggests to the user that the customary finely-divided polishing agent may be absent and for this reason he may regard the composition as an inferior dentifrice to those of the common opaque paste variety.

We also surprisingly found a significant improved cleaning effect was obtained with oral hygiene compositions containing such large particle size xerogels compared with the compositions disclosed in the aforesaid patent specification.

We have accordingly found that silica xerogels of average particle size diameter at least 25 and in the range of from 25 to 50, preferably from 25 to 30, microns are new cleaning and polishing agents for use in improved oral hygiene compositions.

Accordingly, the present invention provides an oral hygiene composition containing as the sole or principal polishing agent from 1 to 50% by weight of the composition of a silica xerogel having an average particle size diameter of from 25 to 50, preferably from 25 to 30, microns.

The silica xerogel is a particulate, synthetic, amorphous and porous form of silica that is prepared by slow evaporation of water from a silica hydrogel, for example by hot air drying, until the desired average particle size has been reached, but not exceeded. If desired the formed xerogel can be admixed with a silica xerogel of lower average particle size provided that the average particle size diameter, that is the average weight median diameters of the particles, of the silica xerogel mixture is within the stated range for the present invention.

The silica hydrogel is itself prepared by the addition of weak alkali metal silicate to a dilute acid solution which is then allowed to set into a gel, as described in U.S. Pat. No. 3,528,230 and British patent specification No. 1,186,706.

In the latter specification considerable emphasis is laid on the specific surface area of the silica xerogel used, it being stated that this should be at least 600 square meters per gram, preferably about 700 square meters per gram. We have found that this is not such an important criterion and that silica xerogels with specific surface areas of from 250 to 800 square meters per gram may be employed, provided that the xerogel has an average particle size diameter within the stated range. Preferably the silica xerogel employed has a particle density of 1.00–1.20g./cc.

While the oral hygiene compositions of the invention can be in any of the usual forms and contain any of the conventional dentifrice ingredients and in particular will normally contain a surfactant, very suitable compositions are those of the translucent gel type exemplified by the dentifrices described in U.S. Pat. No. 3,528,230 and British patent specification No. 1,186,706. Such compositions will usually contain at least 3% by weight, preferably from about 5 to about 20%, of the silica xerogel polishing agent. However the larger size xerogel particles described above also find use in oral hygiene compositions which are liquid dentifrices of the mouthwash type. In such compositions the liquid medium is one that does not result in a gel type product. Nevertheless, the product is preferably a viscous, though flowable, liquid suitable for use as a mouthwash and this is achieved by the use of higher proportions of liquid media that is more viscous than water, particularly by the use of high proportions of sorbitol, glycerol and the like.

If a dentifrice composition of the translucent gel type is desired, the dentifrice compositions of the invention may contain, in addition to the above-described silica xerogel from 0.5 to 20%, and preferably from 2 to 15% by weight of the dentifrice, of a synthetic silica which has thickening and gelling properties. Such particulate synthetic silicas have an average particle diameter below 4 microns and a surface area of less than 400 square meters per gram. Examples include pyrogenic silicas and silica aerogels. These silicas do not remove the stains from teeth.

Small amounts up to about 10% by weight of the dentifrice of conventional dental abrasives, such as water-insoluble sodium metaphosphate, can be included.

The oral hygiene compositions of the invention can also contain various optional ingredients as is well-known to those skilled in the art of formulating dentifrice compositions. For instance these may be included: a soap or synthetic detergent, especially sodium lauryl sulphate in amounts of from about 1.05% to about 2.0% of the composition, as foaming or wetting agent; flavouring materials; buffers; sweeteners, such as saccharin; humectants; preservatives; colouring materials; opacifying agents, such as titanium dioxide; and powdered polymers such as an alpha-olefin polymer, for example polyethylene.

The oral hygiene compositions may contain a carrier and softener and a binder in amounts to give the dentifrice a smooth texture and good flowability. Glycerol and sorbitol are preferred carriers and softeners, but others, for example propylene glycol and polyethylene glycol, can also be employed. Examples of suitable binders that can be used are gum tragacanth, sodium carboxymethyl-cellulose, hydroxyethyl cellulose, carrageenan and its derivatives, starch derivatives and locust bean gum.

There can also be included in the oral hygiene compositions of the invention prophylactic or therapeutic agents, such as germicides, antibiotics, astringents or fluorine-containing compounds. Typical examples thereof include tyrothrycin, chlorophyllins, hexachlorophene, chlorhexidine, the sarcosinates, astringent salts and water-soluble ionizable fluorine-containing compounds, for example sodium fluoride, stannous fluoride, and sodium mono-fluorophosphate.

Such prophylactic or therapeutic agents are employed in a beneficial amount. In the case of water-soluble anti-cariogenic fluorine-containing compounds such amount will normally provide the composition with a fluorine content of from 0.01 to 2%. The carriers and softeners are generally employed in an amount from 5 to 30%, the binders in an amount from 0.5 to 30%, flavouring agents in an amount from 0.1 to 5%, water in an amount up to 60% by weight of the composition, foaming agents in an amount from 0.01 to 6%, buffers in an amount from 0.02 to 10%, and preservatives in an amount from 0.01 to 2%, all percentages being by weight of the oral hygiene composition.

The present compositions are formulated in conventional manner, that is the silica xerogel (of defined particle size) is mixed with diluents, supportants and any other ingredients desired, to prepare the oral hygiene composition which may be packaged into tubes or other appropriate dispensers.

The invention is illustrated by the following Examples which are specific oral hygiene formulations. Examples 1-6 illustrate such formulations each in the form of a transparent or translucent gel. The silica xerogel, silica CM, had an average particle size diameter of about 25 microns and a specific surface area of 675 square meters per gram. The silica aerogel was that sold by W. R. Grace & Co. under the trade mark SYLOID 244. In Example 6, 5% of the aforesaid silica xerogel was admixed with 2% of a commercially available silica xerogel, SYLOID 63, which has an average particle size diameter of 12 microns and a specific surface area of 800 m²/g, but in such proportions that the average particle size diameter of the total xerogel mixture is at least 25 microns.

The abrasive properties of the formulated dentifrice compositions of the invention were determined by two methods. In the Talysurf method the root of an extracted tooth is embedded in a resin block so that its surface can be ground flat and so that it can be accurately located in the "Talysurf 4" surface profile measuring instrument which draws a magnified cross-section of the tooth surface (horizontal magnification × 100, vertical magnification × 200). When the initial flatness of the mounted tooth is satisfactory, it is transversely brushed with a single toothbrush tuft in a machine operating under standard conditions (which cover length of stroke, speed of stroke, dilution of toothpaste, temperature, pre-conditioning of tuft, load on tuft, degree of stirring, etc.), such that the toothpaste slurry is the only variable. After 1000 strokes the tooth surface is again measured on the "Talysurf" instrument and, by comparison with the initial measurement, the abraded cross-sectional area is determined which represents the abrasive wear caused by brushing with the toothpaste used in the test.

The figure given from the test represents the volume of dentin removed during the test. Values from this method of up to 40 can be regarded as quite safe with respect to abrasivity. Indeed some commercially available dentifrices give higher values in the "Talysurf" test than this. Dentifrice formulations of the type described in U.S. Pat. No. 3,538,230 normally give Talysurf values within the range 5-20 units.

The "RDA" value is obtained by first irradiating extracted teeth in a neutron flux to make them radioactive and then brushing a dentin surface of the tooth, under standard conditions of brushing, and determining the radioactivity of the slurry surrounding the teeth after their removal. Presently commercially available dentifrices have RDA values up to 450 units so that any value less than this can be considered tolerable.

The results of both abrasion tests are given in the following table and this shows that the abrasive effect of the compositions of the invention is well within acceptable limits. In each case a good cleansing effect was obtained.

EXAMPLES 1-6

| Ingredient | Example (parts by weight) | | | | | |
|---|---|---|---|---|---|---|
| | 1 | 2 | 3 | 4 | 5 | 6 |
| Silica xerogel (Silica CM) | 3.00 | 5.00 | 7.50 | 10.00 | 14.00 | 5.00 |
| Silica xerogel (Syloid 63) | — | — | — | — | — | 2.00 |
| Silica aerogel (Syloid 244) | 7.50 | 9.00 | 7.50 | 7.50 | 7.50 | 9.00 |
| Sodium carboxymethyl-cellulose | 1.25 | 1.45 | 1.00 | 1.25 | 1.25 | 1.45 |
| Glycerol | 30.00 | 22.00 | 30.00 | 30.00 | 30.00 | 21.00 |
| Sorbitol (70%) | 34.05 | 48.33 | 34.30 | 31.55 | 31.55 | 47.33 |
| Sodium saccharin | 0.20 | 0.20 | 0.20 | 0.20 | 0.20 | 0.20 |

-continued

| | Example (parts by weight) | | | | | |
|---|---|---|---|---|---|---|
| | 1 | 2 | 3 | 4 | 5 | 6 |
| Sodium benzoate | 0.20 | 0.20 | 0.20 | 0.20 | 0.20 | 0.20 |
| Sodium lauryl sulphate | 1.15 | 1.50 | 1.15 | 1.15 | 1.15 | 1.50 |
| Flavouring | 1.15 | 1.22 | 1.15 | 1.15 | 1.15 | 1.22 |
| Polyvinyl pyrrolidone | — | 0.10 | — | — | — | 0.10 |
| Chloroform | 1.00 | — | 1.00 | 1.00 | 1.00 | — |
| Water | 20.50 | 11.00 | 16.00 | 16.00 | 12.00 | 11.00 |
| | 100.00 | 100.00 | 100.00 | 100.00 | 100.00 | 100.00 |
| Abrasion Test Results | | | | | | |
| Talysurf | 5.4 | 7.0 | 8.8 | 7.4 | 9.4 | 5.6 |
| RDA | 89 | 133 | 143 | 217 | 279 | 141 |

EXAMPLES 7-9

Liquid oral hygiene compositions were formulated from the following ingredients:

| | Example 7 | Example 8 | Example 9 |
|---|---|---|---|
| | (% by weight) | | |
| Silica xerogel (Silica CMS) | 5.00 | 10.00 | 15.00 |
| Silica aerogel (Syloid 244) | 5.00 | 5.00 | 5.00 |
| Sodium carboxymethyl cellulose | 0.30 | 0.30 | 0.40 |
| Glycerol | 7.00 | 6.00 | 5.00 |
| Sorbitol (70%) | 74.00 | 70.75 | 66.65 |
| Sodium saccharin | 0.20 | 0.20 | 0.20 |
| Sodium benzoate | 0.20 | 0.20 | 0.20 |
| Flavour and colour | 1.70 | 1.70 | 1.70 |
| Sodium lauryl sulphate | 1.50 | 1.15 | 1.15 |
| Polyvinyl pyrrolidone | 0.10 | 0.10 | 0.10 |
| Water | 5.00 | 4.60 | 4.60 |
| | 100.00 | 100.00 | 100.000 |

The "Silica CMS" xerogel was similar to "Silica CM" in having an average particle size diameter of 25 microns, but (unlike Silica CM) it did not contain any particles with diameters larger than 60 microns. Each composition was a clear, flowable, viscous, liquid dentifrice with satisfactory teeth cleaning and abrasive properties.

EXAMPLES 10-13

Further dentifrices according to the invention were formulated from the following ingredients:

| | Example (parts by weight) | | | |
|---|---|---|---|---|
| Ingredient | 10 | 11 | 12 | 13 |
| Silica xerogel (Silica CM) | 1.00 | 2.50 | 5.00 | 14.00 |
| Silica aerogel (Syloid 244) | 5.00 | 5.00 | 8.50 | 7.50 |
| Sodium carboxymethyl cellulose | 0.70 | 0.60 | 1.00 | 0.60 |
| Glycerol | 7.00 | 7.00 | 5.53 | 5.53 |
| Sorbitol (70%) | 76.75 | 75.35 | 75.79 | 68.19 |
| Calcium carrageenan | 0.10 | 0.10 | — | — |
| Sodium saccharin | 0.25 | 0.25 | 0.20 | 0.20 |
| Sodium benzoate | 0.20 | 0.20 | 0.08 | 0.08 |
| Sodium lauryl sulphate | 2.00 | 2.00 | 1.47 | 1.47 |
| Flavouring | 1.50 | 1.50 | 1.15 | 1.15 |
| Chloroform | — | — | 0.75 | 0.75 |
| Water | 5.50 | 5.50 | 0.53 | 0.53 |
| | 100.00 | 100.00 | 100.00 | 100.00 |

The cleaning effect of the gel compositions of Examples 12 and 13 was compared with a commercially available paste of the translucent gel type made according to U.S. Pat. No. 3,538,230 and containing a silica xerogel having an average particle size diameter of about 12 microns.

For the cleaning tests specimens of human teeth were selected in which the enamel contained uncalcified stains on smooth, undecalcified, slightly curved enamel surfaces. Cylinders of enamel were then cut with a coring tool and mounted in black plastic. The optical density of a specimen was read and the specimen was then brushed with one of the test products. This resulted in stain removal and subsequent change in the optical density of the specimen. This procedure was carried out for each dentifrice being tested, making changes in sequence and specimen used in order to ensure that all variable were standardized. The raw data is recorded as optical density × 100 per minute of brushing. This data is then corrected for test order by adjusting the sums for the first and third runs to equal that of the second run. This is done by taking the sum for each test (1, 2 and 3) for each dentifrice and obtaining the total for each test. The total for the test (1 or 3) is then divided into the total for test 2 and this result is the factor by which all numbers in tests 1 and 3 are multiplied to obtain the corrected data. In this way the effect of test order is ruled out.

The totals of the six values, obtained in this way for each of the three dentifrices obtained by this comparative stain removal test were:

| Dentifrice | Talysurf | Total for decrease in optical density × 100 per minute of brushing | RDA |
|---|---|---|---|
| Example 12 | 3.8 | 31 | 93 |
| Example 13 | 8.4 | 30 | 217 |
| Comparative Formulation | 11.1 | 6 | 241 |

Thus the compositions of the invention have been shown to give improved cleaning effect over compositions in which the silica xerogel employed was of smaller average particle size. Increasing the amount of xerogel from 5 to 14% produced no significant change in cleaning effect.

We claim:

1. An oral hygiene composition in the form of a translucent dentifrice gel consisting essentially of: (a) from about 3 to about 14% of a silica xerogel of average particle size diameter of 25-30 microns; (b) from about 5.0 to about 10% of silica aerogel; (c) from about 1.0 to about 1.5% of sodium carboxymethylcellulose; (d) from about 20 to about 30% of glycerol; (e) from about 20 to about 50% of sorbitol; and (f) from about 1.05 to about 2.0% of sodium lauryl sulphate, the balance being water and agents for flavouring, sweetening and thickening said composition and providing it with anti-corrosive properties.

2. An oral hygiene composition in the form of a translucent dentifrice gel having as its sole or principal polishing agent 5 to 20% by weight of the composition of a silica xerogel of average particle size in diameter in the range of 25-50 microns with a particle density of 1.00-1.20 g/cc.

3. An oral hygiene dentifrice composition according to claim 2, wherein the silica xerogel average particle size diameter is about 25-30 microns and the composition has a Talysurf value between 3.8 and 9.4 and an RDA value between 89 and 279.

4. A transparent or translucent gel dentifrice having as its sole or principal polishing agent 1-15 parts by weight of the composition of silica xerogel of average particle size diameter in the range of 25–30 microns and characterized by a cleaning action on human teeth significantly greater than silica xerogel particles of smaller average micron particle size diameter, 5–9 parts by weight of the composition of silica aerogel, and small effective amounts of a humectant, thickener, synthetic sweetener, flavouring, colorant and preservative agent with the balance being 11–20.50 parts by weight of the composition of water to make 100.00 parts, and the dentifrice owing its greater cleaning effect as compared with the particles of smaller average micron particle size diameter to the said average micron particle size diameter of 25–30 microns with decreased abrasion and scratching action on the enamel of teeth cleaned therewith.

5. A gel dentifrice according to claim 4 wherein the silica xerogel has an average particle size diameter of about 25 microns.

6. An oral hygiene composition in the form of a viscous liquid dentifrice consisting essentially of: (a) from about 1 to about 15% of a silica xerogel of average particle size diameter in the range of 25–20 microns; (b) from about 5 to about 8.5% of silica xerogel; (c) from about 0.3 to about 1.0% of sodium carboxymethylcellulose; (d) from about 5 to about 7% of glycerol; (e) from about 45 to about 90% of sorbitol; and (f) from about 1.0 to about 2.0% of sodium lauryl sulphate, the balance being water and agents for flavouring, sweetening and thickening said composition and providing it with anti-corrosive properties.

* * * * *